United States Patent [19]

Smith

[11] Patent Number: 5,669,885
[45] Date of Patent: Sep. 23, 1997

[54] TROCAR ASSEMBLY WITH SPRING-LOADED MECHANISM

[75] Inventor: Robert C. Smith, Danbury, Conn.

[73] Assignee: United States Surgical Corporation, Norwalk, Conn.

[21] Appl. No.: 645,885

[22] Filed: May 14, 1996

[51] Int. Cl.$^6$ .................................... A61B 17/32
[52] U.S. Cl. .................. 606/184; 604/164; 30/366
[58] Field of Search .......................... 606/184, 185; 604/160, 161, 164, 165, 185, 188, 264; 128/751–753; 30/151, 152, 162, 366–368

[56] References Cited

U.S. PATENT DOCUMENTS

| | | |
|---|---|---|
| 1,248,492 | 12/1917 | Hill . |
| 1,640,311 | 8/1927 | Dawes . |
| 2,623,521 | 12/1952 | Shaw . |
| 4,094,217 | 6/1978 | Exline . |
| 4,256,119 | 3/1981 | Gauthier . |
| 4,527,561 | 7/1985 | Burns . |
| 4,535,773 | 8/1985 | Yoon . |
| 4,601,710 | 7/1986 | Moll . |
| 4,747,831 | 5/1988 | Kulli . |
| 4,767,413 | 8/1988 | Haber et al. . |
| 4,813,426 | 3/1989 | Haber et al. . |
| 4,817,631 | 4/1989 | Schnepp-Pesch et al. . |
| 4,874,382 | 10/1989 | Lindemann et al. . |
| 4,904,242 | 2/1990 | Kulli . |
| 4,946,446 | 8/1990 | Vadher . |
| 4,973,316 | 11/1990 | Dysarz . |
| 5,046,508 | 9/1991 | Weissler . |
| 5,066,288 | 11/1991 | Deniega et al. . |
| 5,116,353 | 5/1992 | Green . |
| 5,462,532 | 10/1995 | Gresl ........................... 606/185 |
| 5,522,833 | 6/1996 | Stephens et al. . |
| 5,527,335 | 6/1996 | Bolduc et al. ................ 606/185 |

OTHER PUBLICATIONS

"Needle for the Puncture and Lavage of the Abdominal Cavity" by F.S. Zubairov.

Primary Examiner—William Lewis

[57] ABSTRACT

A novel safety trocar assembly includes a cannula having a cannula housing with a cannula sleeve and an obturator assembly which includes (i) an obturator housing, (ii) an obturator sleeve connected to the obturator housing, (iii) an elongated obturator portion at least partially disposed within the obturator sleeve and having a penetrating distal tip for penetrating tissue, and (iv) a protective guard coaxially mounted about the penetrating tip. The obturator portion is longitudinally moveable between a disarmed position wherein the penetrating tip is contained within the cannula sleeve and an armed position wherein the penetrating tip at least partially extends beyond the distal end of the cannula sleeve. The protective guard of the obturator assembly is moveable relative to the penetrating tip between an extended position enclosing the penetrating tip and a retracted position exposing the penetrating tip for penetrating action.

16 Claims, 10 Drawing Sheets

TROCAR ASSEMBLY WITH SPRING-LOADED MECHANISM

BACKGROUND

1. Field of the Disclosure

The present disclosure relates generally to trocar assemblies for use in endoscopic surgical procedures and, in particular, to a trocar assembly incorporating a mechanism to minimize the possibility of inadvertent injury to viscera and other internal tissue during use.

2. Description of the Related Art

Endoscopic surgical procedures, that is, surgical procedures performed through tubular sleeves or cannulas, have been increasingly accepted as the preferred treatment for ailments traditionally treated via conventional surgical techniques. Initially, endoscopic surgical procedures were primarily diagnostic in nature. More recently, however, as endoscopic technology has advanced, surgeons are performing increasingly complex and innovative surgical procedures using endoscopic principles. In endoscopic procedures, surgery is performed in any hollow viscus of the body through a small incision or through narrow endoscopic tubes (cannulas) inserted through small entrance wounds in the skin. Endoscopic procedures require the surgeon to act on organs, tissues and vessels far removed from the incision, thereby requiring that any instruments to be used in such procedures be sufficient in size and length to permit remote operation.

Laparoscopic surgery is a type of endoscopic surgery in which the surgical procedures are performed in the interior of the abdomen. In accordance with laparoscopic techniques, the surgical region, e.g., abdominal cavity, is insufflated with a gas such as $CO_2$ to raise the cavity wall away from the internal organs therein. Thereafter, a trocar is used to puncture the body cavity. Generally, a trocar includes an obturator having a sharp penetrating tip disposed within a protective tube or sleeve. The trocar is typically used with, or incorporates, a cannula having a cannula sleeve which remains within the incision subsequent to removal of the obturator. The cannula defines a port for the insertion of surgical instruments required to perform the desired surgery. An example of a known trocar is described in commonly assigned U.S. Pat. No. 4,601,710 to Moll.

Recent developments in the design of surgical trocars include the provision of safety mechanisms to ensure that the distal penetrating tip is covered or enclosed once the body cavity has been penetrated, thereby providing an increased level of protection to internal structures from undesired puncture or laceration. Examples of safety trocars are disclosed in U.S. Pat. Nos.: 3,030,959 to Grunert; 3,657,812 to Lee; 4,375,815 to Burns; 4,535,773 to Yoon; 4,601,710 to Moll; and 5,116,353 to Green.

SUMMARY

The present disclosure is directed to further improvements in the design of safety trocars. In one preferred embodiment, the novel trocar assembly includes a cannula assembly having a cannula housing with a cannula sleeve and an obturator assembly which includes (i) an obturator housing, (ii) an obturator sleeve connected to the obturator housing, (iii) an elongated obturator portion at least partially disposed within the obturator sleeve and having a penetrating distal tip for penetrating tissue, and (iv) a protective guard coaxially mounted about the penetrating tip. The obturator portion is longitudinally moveable between a disarmed position wherein the penetrating tip is contained within the cannula sleeve and an armed position wherein the penetrating tip and at least the distal end portion of the protective guard extend beyond the distal end of the cannula sleeve. The obturator portion is normally biased to the disarmed position.

Means are provided to retain the obturator portion in the armed position. The preferred retaining means is in the form of a latch mechanism having a latch mounted to the obturator portion and being configured and dimensioned to engage corresponding structure, e.g. a locking shelf of the obturator sleeve, to maintain the obturator portion in the armed position.

Release means are also provided for releasing the retaining means to permit the obturator portion to return to the disarmed position. The preferred release means includes a pawl mechanism having a pawl which engages and displaces the latch from its engagement with the internal shelf of the obturator sleeve. The release means is actuated upon removal of a counterforce applied to the penetrating tip, i.e., upon entering through the body tissue.

The protective guard of the obturator is moveable relative to the penetrating tip between an extended position enclosing the penetrating tip and a retracted position exposing the penetrating tip for penetrating action. The protective guard is normally spring biased to the extended position and moves to the retracted position in response to a counterforce exerted by tissue on the protective guard during insertion through the tissue.

In use of the trocar assembly, the obturator portion is placed in its armed position thereby advancing the penetrating tip and protective guard at least partially beyond the cannula sleeve. Once in the armed position, the obturator portion is retained in said position by the latch mechanism of the retaining means. The penetrating tip is placed against tissue whereby the counterforce exerted by the tissue causes the protective guard to retract to expose the penetrating tip. When the penetrating tip clears the tissue (thus resulting in the removal of the counterforce), the protective guard assumes its normal extended position enclosing the penetrating tip. Concurrently therewith, the removal of the counterforce activates the release means thereby causing the obturator portion to assume its non-deployed position.

BRIEF DESCRIPTION OF THE DRAWINGS

Preferred embodiment(s) of the disclosure are described hereinafter with reference to the drawings wherein.

DETAILED DESCRIPTION OF THE PREFERRED EMBODIMENTS

Figure 1:
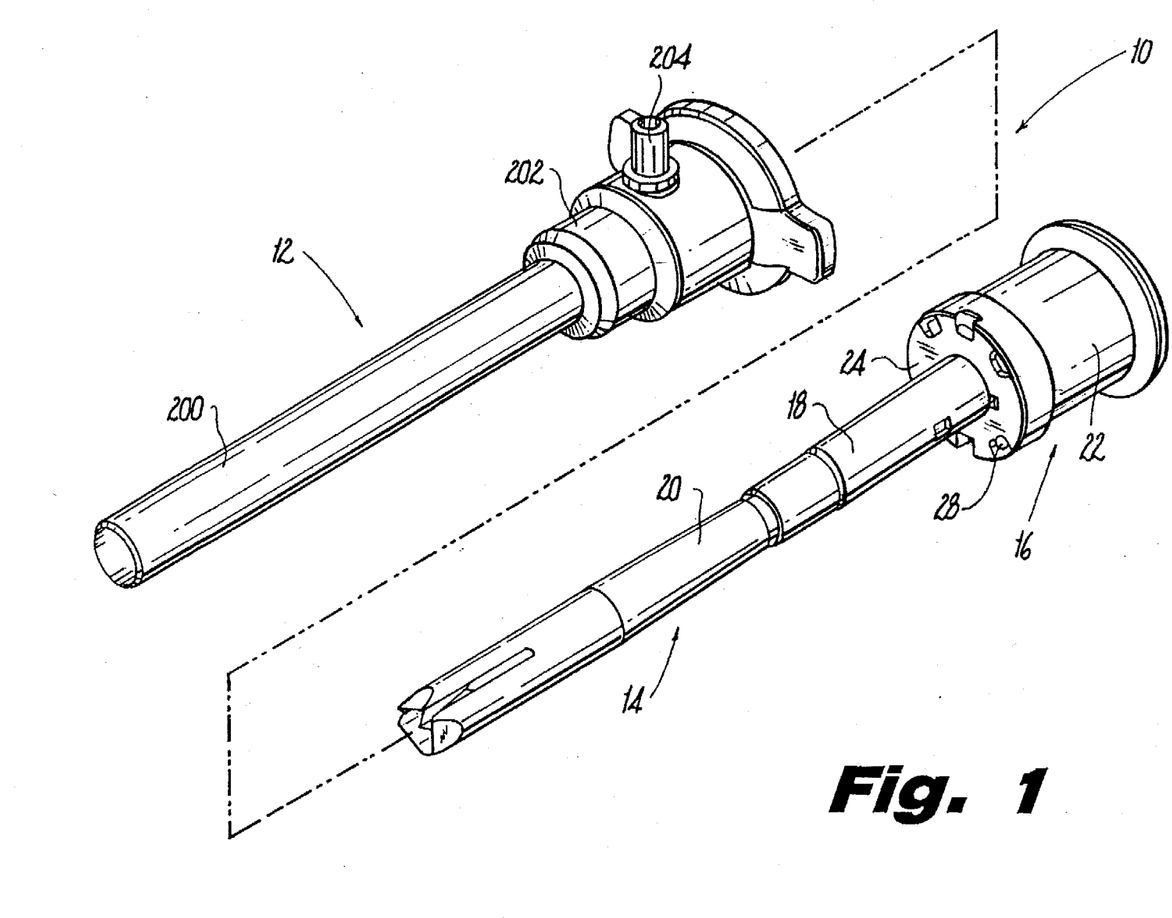
FIG. 1 is a perspective view of the trocar assembly of the present disclosure illustrating the obturator assembly and cannula assembly.

Referring now in specific detail to the drawings, in which like reference numerals identify similar or like components throughout the views, FIG. 1 illustrates in perspective view the trocar assembly in accordance with the principles of the present disclosure. The trocar assembly 10 is intended to be used in laparoscopic surgery where insufflation gases are introduced into the peritoneal cavity to raise the cavity wall away from the internal organs therein. Trocar assembly 10 includes a cannula assembly 12 and an obturator assembly 14 which is positionable within the cannula assembly 12. The term "obturator assembly" as used herein refers to the tissue penetrating portion of the trocar assembly 10.

Figures 2, 3:
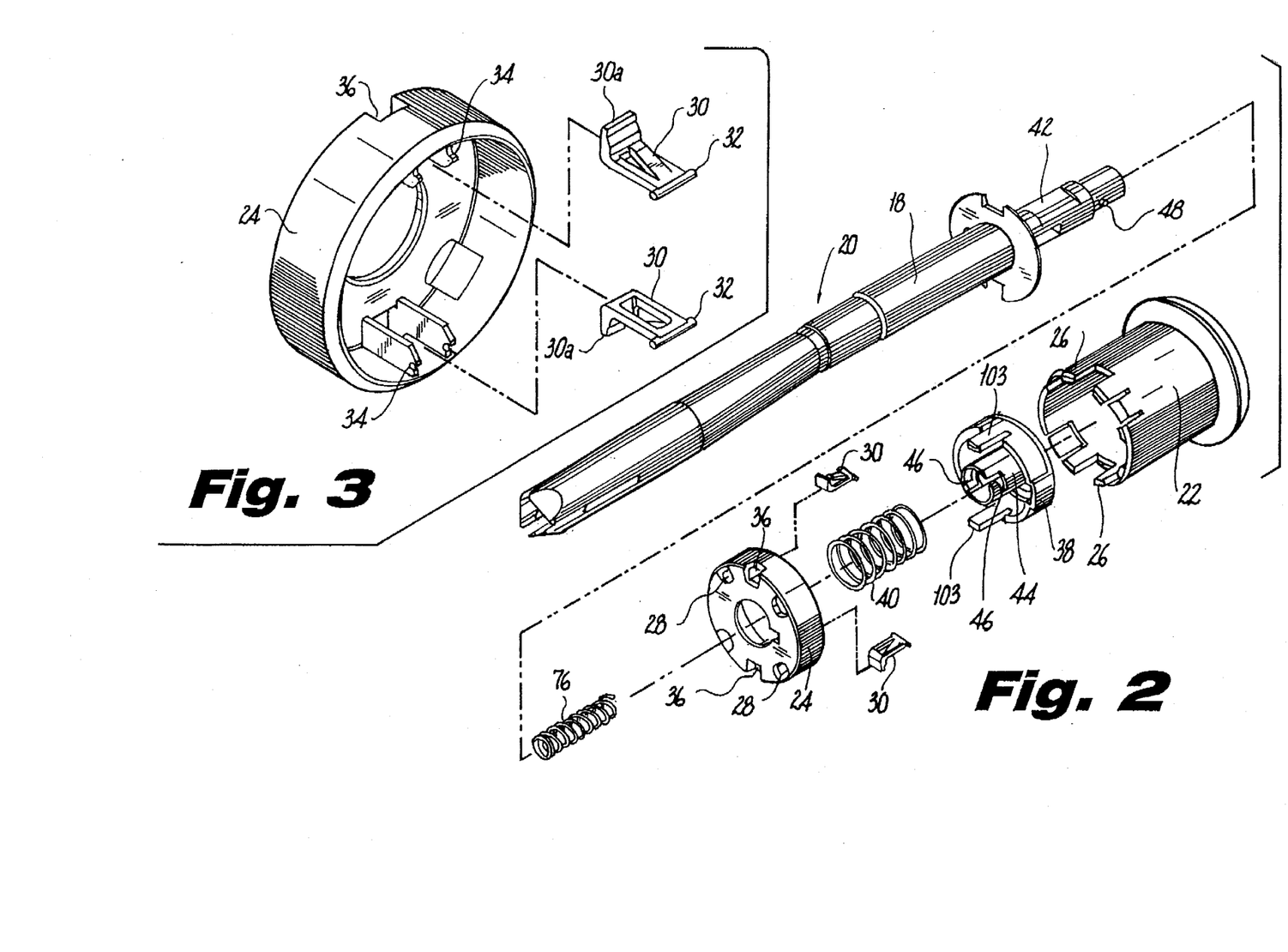
FIG. 2 is a perspective view with parts separated of the obturator assembly illustrating the obturator housing, the obturator sleeve and the elongated obturator portion disposed within the obturator sleeve.
FIG. 3 is a perspective view illustrating the locking collar of the obturator housing for releasably mounting the obturator assembly to the cannula assembly.

Referring now to FIGS. 1 and 2, obturator assembly 14 will be discussed in detail. Obturator assembly 14 includes obturator housing 16, obturator sleeve 18 connected to and extending from the housing 16 and obturator portion 20 which is at least partially disposed within the obturator sleeve 18. Obturator housing 16 includes frame or base 22 which is of sufficient size to be grasped by the hands of the user and locking collar 24 mounted to the distal end of the base 22. In a preferred mounting arrangement of base 22 and locking collar 24, the base 22 includes a plurality of circumferentially disposed resilient tabs 26 which are received within correspondingly dimensioned and positioned apertures 28 defined in the perimeter of the locking collar 24 to effectuate the mounting. Other means for mounting base 22 and locking collar 24 are envisioned as well such as with the use of adhesives or the like. It is also contemplated that base 22 and locking collar 24 may be a single unit.

With particular reference to FIGS. 2-3, housing 16 also includes a latch lock arrangement for releasably mounting the obturator assembly 14 to the cannula assembly 12. The latch lock arrangement consists of two diametrically opposed latches 30 pivotally mounted to locking collar 24 through the cooperation of integrally formed pivot pins 32 of the latches 30 with internal mounting slots 34 defined in the locking collar 24. Latches 30 are biased radially outwardly through latch openings 36 defined in locking collar 24 upon advancement of obturator portion 20 to engage corresponding structure of cannula assembly 12, thus, mounting the obturator assembly 14 to the cannula assembly 12. This particular mounting arrangement is disclosed in commonly assigned Ser. No. 08/407,342, filed Mar. 20, 1995, the contents of which are incorporated herein by reference.

Figure 4:
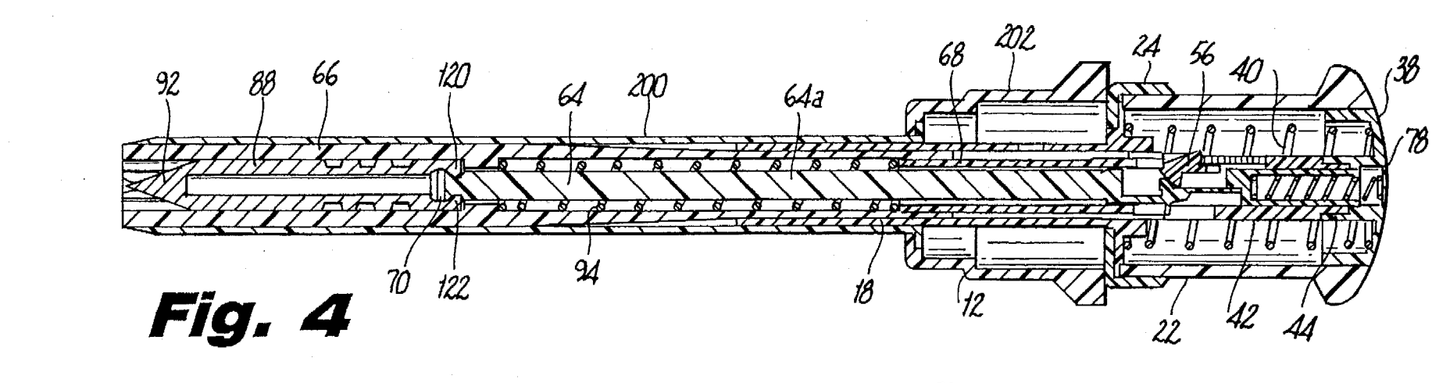
FIG. 4 is a side cross-sectional view of the assembled trocar assembly illustrating the obturator portion in the disarmed position.
Figure 5:
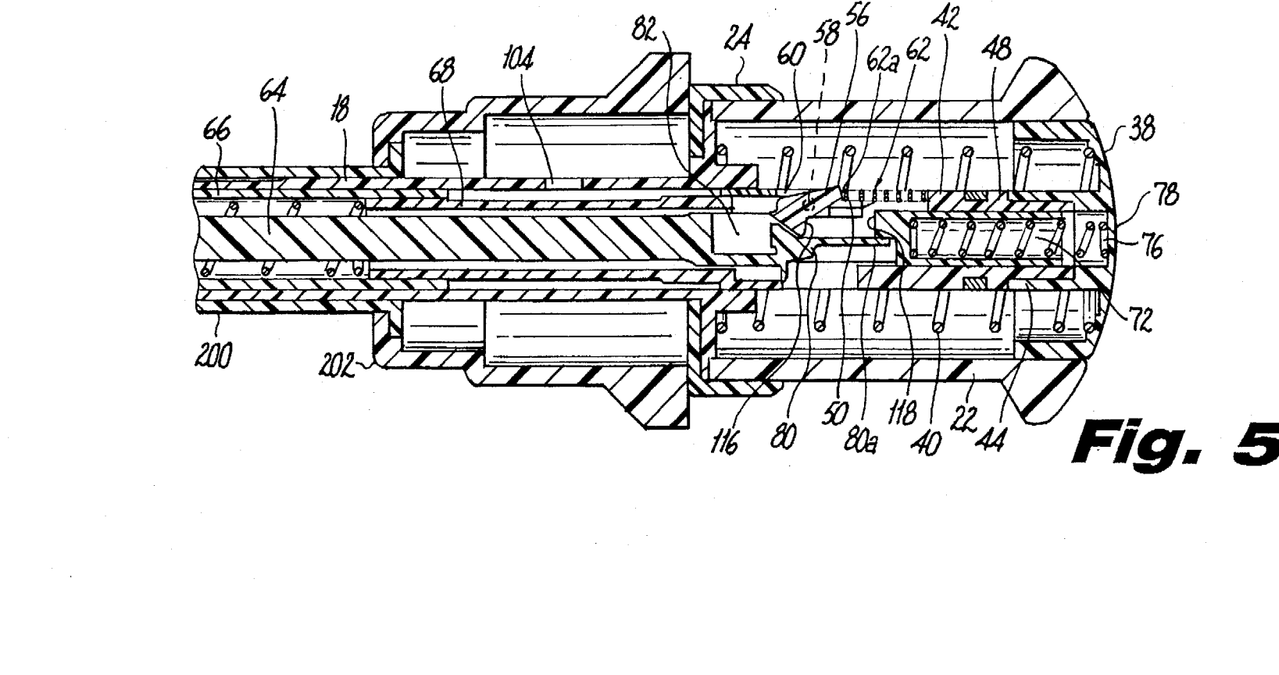
FIG. 5 is an enlarged cross-sectional view of the obturator housing and cannula housing illustrating the latch mechanism for releasably retaining the obturator portion in an armed position.

Referring now to FIGS. 4-5, in conjunction with FIG. 2, obturator assembly 14 further includes, from proximal to distal, actuating button 38, obturator return spring 40 and latch collar 42. Actuating button 38 includes an internal cylindrical collar portion 44 possessing opposed bayonet-type locking slots 46 as best depicted in FIG. 2. Similarly, latch collar 42 has opposed locking pins 48 extending radially outwardly which are received within locking slots 46 to operatively connect actuating button 38 and latch collar 42 in a manner whereby movement of the actuating button 38 causes corresponding translation of the latch collar 42.

Figures 6, 7:
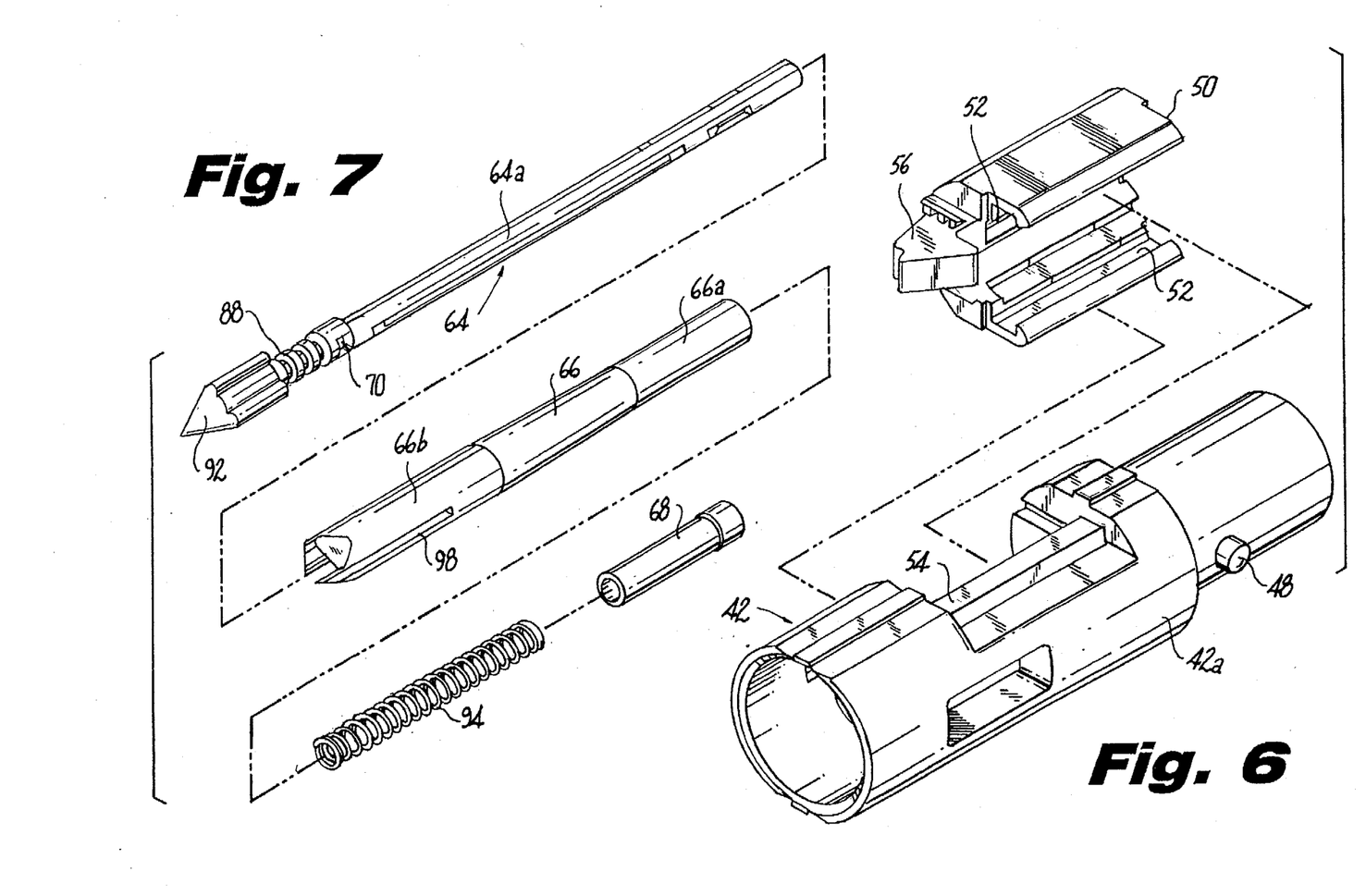
FIG. 6 is a perspective view with parts separated of the latch collar for mounting the latch of the latch mechanism of FIG. 5.
FIG. 7 is a perspective view with part separated of the obturator portion of the obturator assembly illustrating the spring retention collar, the guard biasing spring, the protective guard and the obturator shaft.

Referring now to FIGS. 2, 5 and 6, latch collar 42 has a latch mount 50 which is detachably mounted to the main section 42a of the latch collar 42. In a preferred mounting arrangement, latch mount 50 includes at least two interior longitudinal rails 52 which receive two longitudinal exterior ribs 54 of the main section 42a as best depicted in FIG. 6. Other means for mounting the latch mount 50 to the main section 42a are envisioned as well. Latch mount 50 has a locking latch 56 pivotally mounted along its outer surface about pivot pin 58 (FIG. 5). Latch 56 extends through side opening 60 of latch mount 50. A leaf spring 62 is mounted to latch mount 50 and defines a latch engaging portion 62a which engages the proximal end portion of latch 56 to bias the latch 56 outwardly in a counterclockwise direction with relation to FIG. 5.

Figure 8:
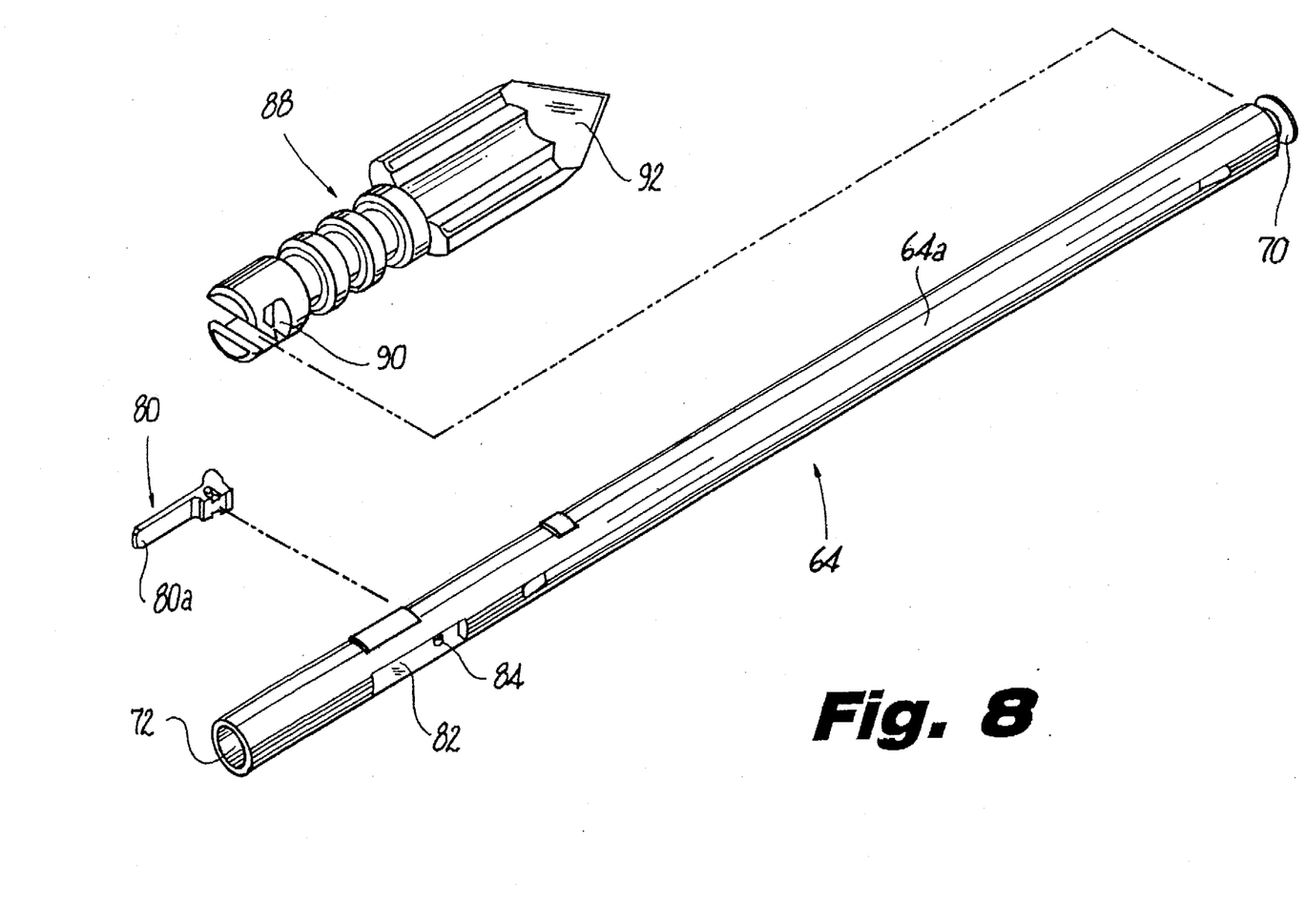
FIG. 8 is a perspective view with part separated of the obturator shaft and the penetrating tip mounted to the obturator shaft.

Referring now to FIGS. 7-8, in conjunction with FIGS. 4-5, obturator assembly 14 includes obturator shaft 64, protective guard or sleeve 66 coaxially mounted about the obturator shaft 64 and spring retention collar 68. Obturator shaft 64 has main shaft portion 64a which extends from within obturator housing 16 and terminates in distal mounting head 70. The proximal end portion of obturator shaft 64 possesses a longitudinal bore 72 which terminates in spring abutment head 74 (FIG. 5). A shaft biasing spring 76 is at least partially disposed in longitudinal bore 72 of obturator shaft 64 and engages at its first end inner surface 78 of actuating button 38 and at its second end abutment head 74 of shaft 64. Biasing spring 76 normally biases obturator shaft 64 distally. Obturator shaft 64 has a resilient pawl 80 which is mounted within a slotted portion 82 of obturator shaft 64 about pin 84. (FIG. 8) Pawl 80 has a proximal end 80a which engages inner horizontal shelf 86 of obturator shaft 64 to limit counterclockwise motion of the pawl 82 in relation to FIG. 5. Obturator shaft 64 also has distal penetrating member 88 which is mounted to distal mounting head 70 of obturator shaft 64 by the reception of the mounting head 70 within mounting recess 90 defined within the member 88. Penetrating member 88 has a pyramidal-shaped penetrating tip 92 dimensioned to penetrate body tissue with minimal force.

Referring now to FIGS. 4 and 7, protective guard 66 is mounted for reciprocal longitudinal movement relative to obturator shaft 64 and penetrating member 88 between a fully extended position in which the penetrating tip 92 is fully enclosed by the guard 66 and a retracted position in which the penetrating tip 92 is at least partially exposed. A guard biasing spring 94 is disposed within protective guard 66 and is coaxially mounted about obturator shaft 64. Guard biasing spring 94 engages at its first end spring collar 68 and at its second end internal shelf 96 of protective guard 66 and functions in normally biasing the protective guard 66 distally. Protective guard 66 defines a constricted proximal portion 66a and an enlarged distal portion 66b to accommodate penetrating member 88. The distal portion 66b of protective guard 66 has three equidistally spaced slots 98 and defines a generally triangular or pyramidal cross-section which corresponds generally in dimension to the cross-section of the penetrating tip 92 of penetrating member 88.

Referring again to FIG. 1, cannula assembly 12 of trocar assembly 10 will now be described. Cannula assembly 12 includes cannula sleeve 200 and cannula housing 202 mounted on one end of the sleeve. Sleeve 200 defines a cannula passage in its interior for reception of obturator assembly 14 and may be formed of stainless steel or the like. Cannula housing 202 is rigidly secured to the proximal end of sleeve 200 and defines a longitudinal bore for reception and passage of obturator portion 20 of assembly 14. Cannula housing 202 further includes an inner peripheral ledge (not shown) at its proximal end which cooperates with latch locks 30 of obturator housing 16 to securely mount the obturator assembly to the cannula assembly 12. Cannula housing 202 may further include a seal (not shown) to minimize loss of insufflation gases during introduction and removal of the surgical instrument through the cannula assembly 12. A stop clock valve 204 is also provided to permit the passage of insufflation gases through the cannula and into the body cavity.

Operation

Figure 9:
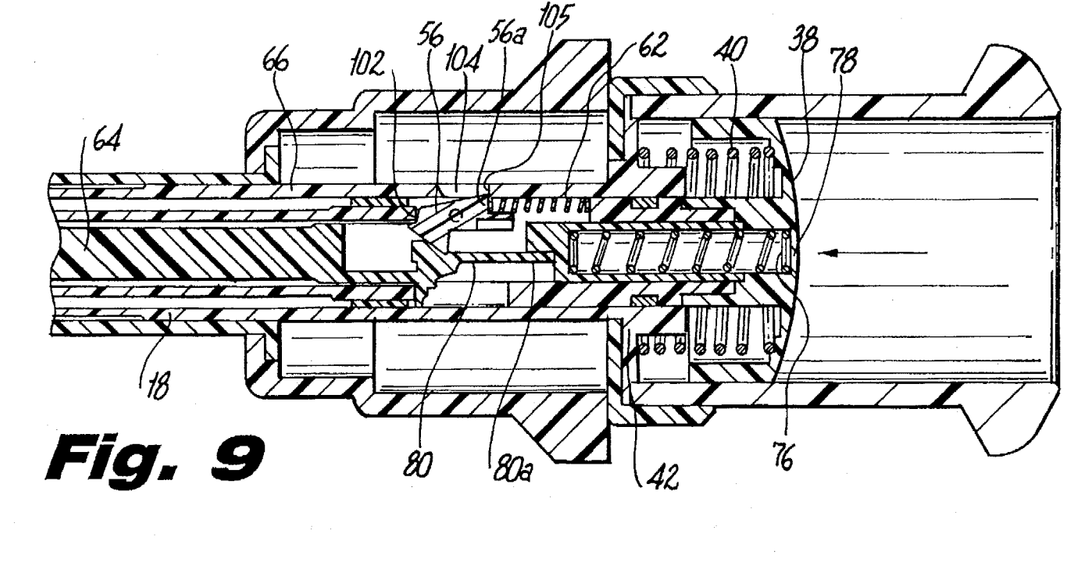
FIG. 9 is a view similar to the view of FIG. 5 illustrating distal advancement of the actuating button to move the obturator portion to the armed position thereof.
Figure 10:
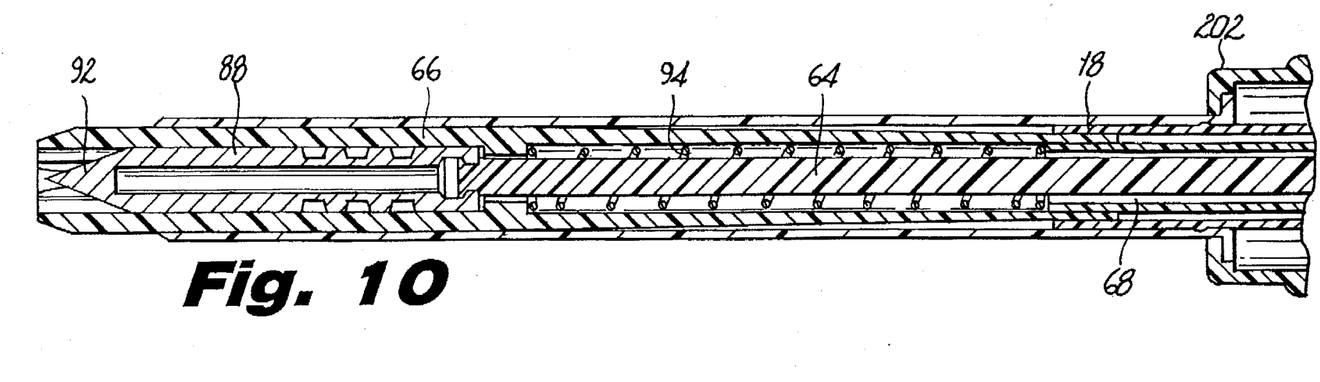
FIG. 10 is a side cross-sectional view illustrating the obturator portion in the armed position.

The operation of trocar assembly 10 will now be discussed. Obturator assembly 14 is positioned within cannula assembly 12 in the manner depicted in FIG. 4. Referring now to FIG. 5, actuating button 38 is distally advanced by depression of the proximal end of the button 38 thereby causing simultaneous distal movement of latch collar 42 and obturator shaft 64. With reference now to FIGS. 9–10, "arming" of the trocar assembly 10 is achieved by further advancing actuating button 38 to its distalmost position shown in FIG. 9. During such movement, latch surface 102 of locking latch 56 engages the proximal end face of spring retention collar 68 to cause simultaneous distal movement of the collar 68. In addition, during advancing movement of actuating button 38, inner camming fingers 103 of the button 38 (FIG. 2) traverse the interior surfaces of locking latches 30 to bias the locking ledge 30a of the locking latch 30 radially outwardly. In the radial outward position, the locking ledges 30a lockingly engage an inner peripheral ledge of cannula housing 202 thereby securing the obturator assembly 14 to the cannula assembly 12.

Once actuating button 38 reaches the "armed" position depicted in FIGS. 9–10, locking latch 56 is received within opening 104 provided in obturator sleeve 18 whereby latch engaging surface 56a engages locking shelf 105 defined by the opening 104 thereby releasably securing actuating button 38 and obturator shaft 64 in the distalmost "armed" position. It is to be noted that leaf spring 62 continually biases locking latch 56 into engagement with the shelf 105. In the "armed" position of obturator assembly 12, penetrating tip 88 and the distal portion of protective guard 66 extend beyond cannula sleeve 202 as depicted in FIG. 10. Protective guard 66 is biased to the extended position under the influence of compression spring 94.

Figure 11:
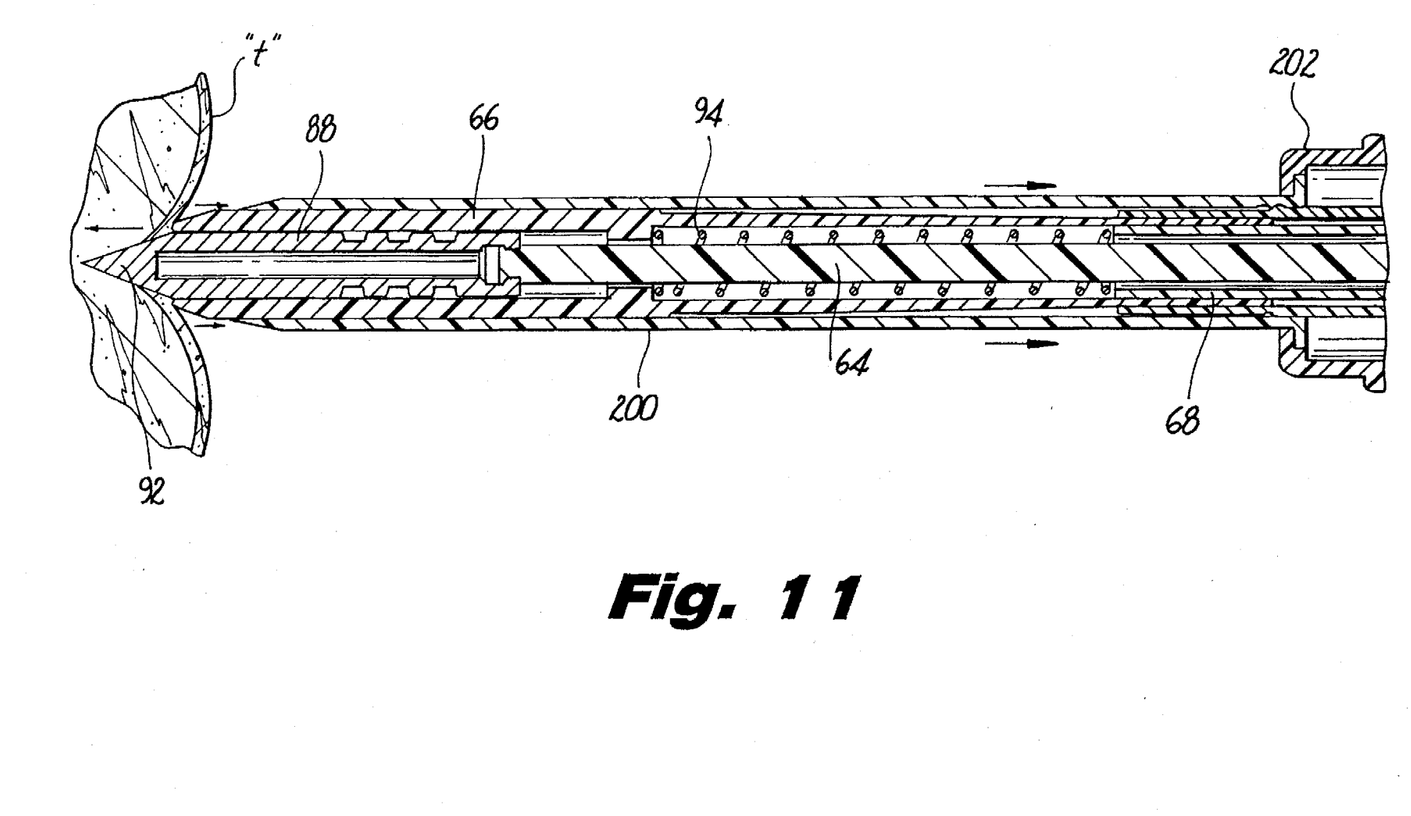
FIG. 11 is a side cross-sectional view illustrating the obturator portion applied against tissue whereby the protective sleeve moves proximally in response to the counterforce exerted by the tissue to expose the penetrating tip.

Referring now to FIG. 11, with the obturator shaft 64 fully extended, the surgeon presses the distal end of the obturator against the body cavity lining "t". The counterforce applied by the tissue causes: 1) protective guard 66 to move proximally against the influence of guard biasing spring 94 from the extended position depicted in FIG. 10 to the retracted position shown in FIG. 11 thereby exposing the penetrating tip 92 for penetrating action; and 2) the penetrating tip 92 and obturator shaft 64 to move proximally against the influence of shaft biasing spring 76 (FIG. 9). It is to be noted that proximal movement of obturator shaft 64 is permitted in the "armed" position of actuating button 38 due to the clearance provided between the proximal end face of the obturator shaft 64 and the interior surface 78 of the button 38.

Figure 12:
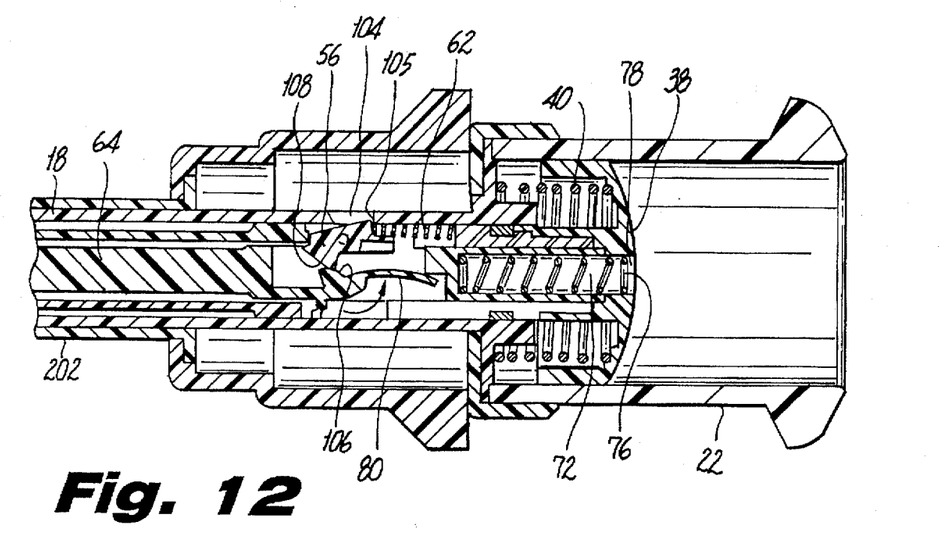
FIG. 12 is a view similar to the view of FIG. 9 illustrating proximal movement of the obturator shaft in response to the counterforce exerted by the tissue on the penetrating tip and the corresponding movement of the latch mechanism.
Figure 13:
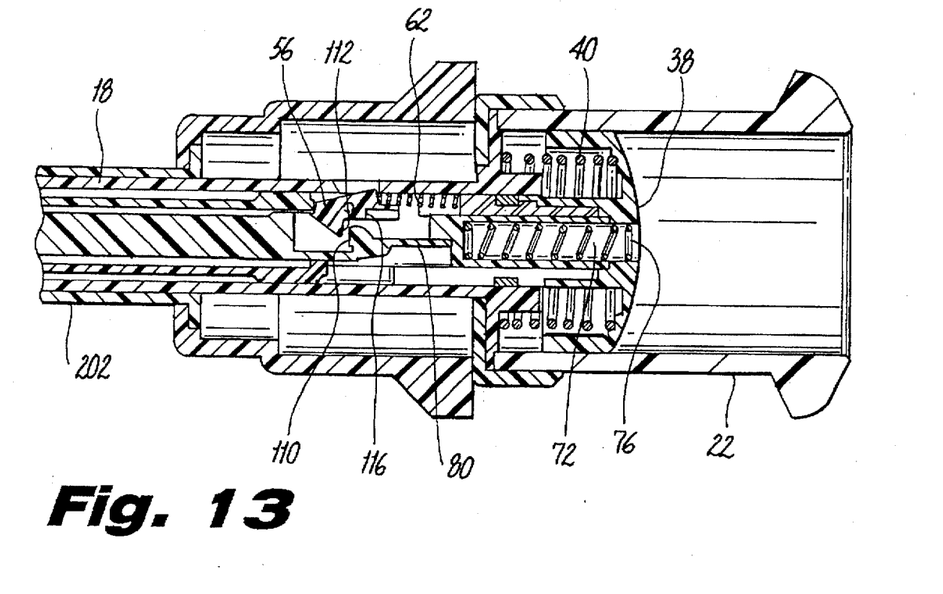
FIG. 13 is a view similar to the view of FIG. 12 illustrating the obturator shaft fully retracted and the corresponding arrangement of the latch mechanism.

With reference to FIGS. 12 and 13, as obturator shaft 64 moves proximally, forward portion 106 of pawl 80 engages inclined surface 108 of locking latch 56 and is driven downwardly by the latch 56 so as to gain clearance thereby. The resilient quality of pawl 80 permits the pawl 80 to flex downwardly and rotate slightly in a counterclockwise direction upon engagement with locking latch 56 as depicted in FIG. 12 to assume the orientation of FIG. 13. FIG. 13 illustrates obturator shaft 64 in its retracted or proximalmost position.

Figure 14:
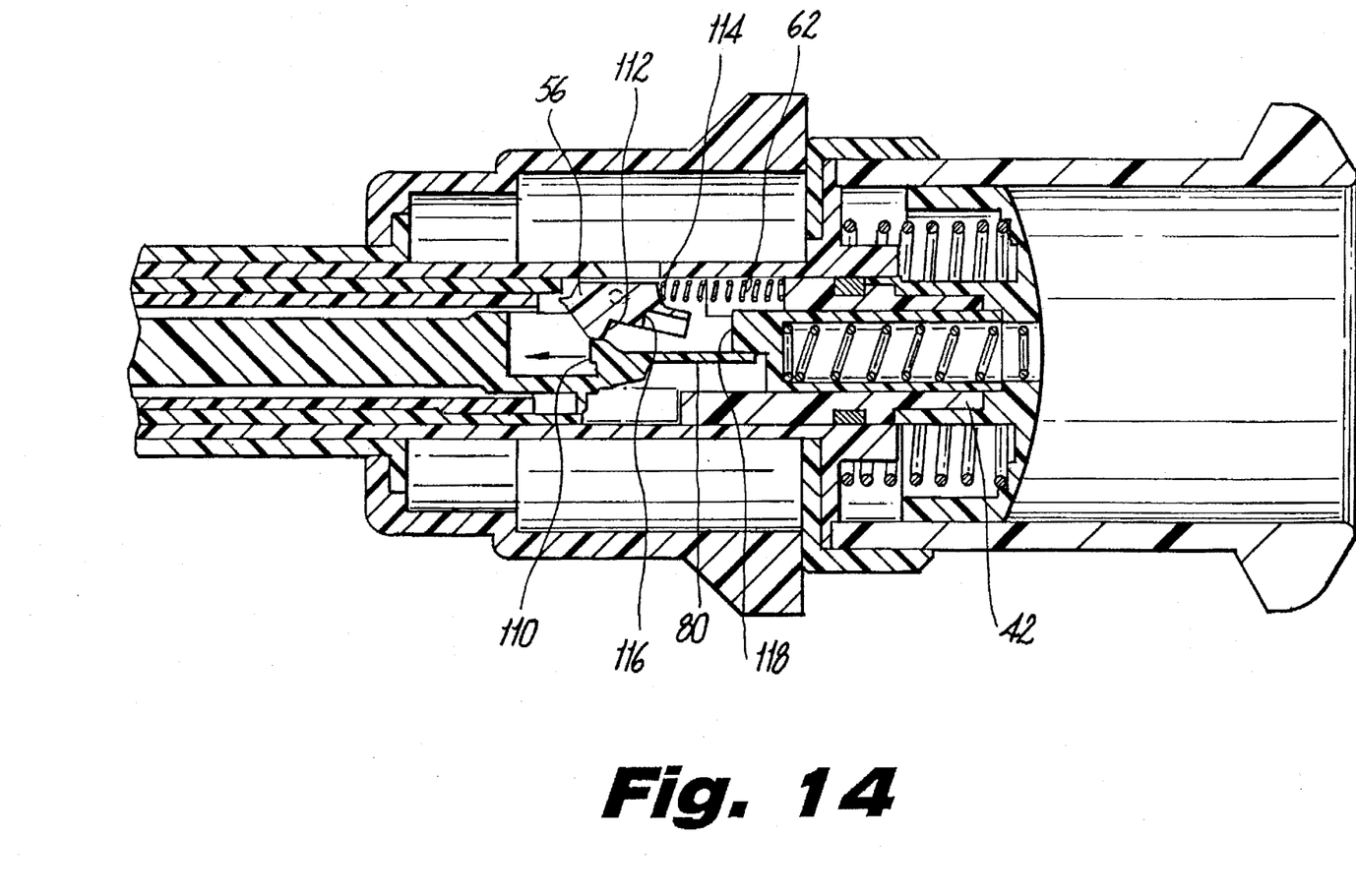
FIG. 14 is a view similar to the view of FIG. 13 illustrating the advancing movement of the obturator shaft when the penetrating tip clear the tissue and the corresponding release of the latch mechanism.

Once the incision is made and as penetrating tip 92 passes through the body tissue, the counterforce applied against penetrating tip 92 by the body tissue ceases. As a result, protective guard 66 is biased distally under the influence of guard biasing spring 94 to cover penetrating tip 92. In addition, the absence of the counterforce permits shaft biasing spring 76 to spring distally to its rest position, thereby biasing obturator shaft 64 distally. With reference to FIG. 14, as obturator shaft 64 moves distally, forward surface 110 of pawl 80 engages shelf 112 of locking latch 56 and causes the latch 56 to rotate in a general clockwise direction against the influence of lever spring 62. This clockwise rotation of locking latch 56 results in clockwise rotation of rear engaging surface 56a thereby freeing the latch 56 from its engagement with internal shelf 105 of obturator sleeve 18.

As soon as latch 56 clears internal shelf 105, there no longer remains any restraint to the return of actuator button 38 to its initial position. Thus, actuator button 38 and latch collar 42 move proximally under the influence of obturator return spring 40. With reference again to FIG. 5, as latch collar 42 moves proximally, vertical surface 116 of locking latch 56 engages inner vertical surface 118 of obturator shaft 64 thereby driving the obturator shaft 64 proximally. Such movement of obturator shaft 64 simultaneously corresponds in proximal movement of protective sleeve 66 through the engagement of forward vertical surface 120 of penetrating member 86 with inner shelf 122 of the protective guard 66 (FIG. 4). This proximal movement of protective guard 66 also drives spring retention collar 68 proximally through the interaction of compression spring 94 with the distal face of the collar 68.

In addition, with actuating button 38 in the proximal inactivated position, mounting latches 30 of locking collar 24 become disengaged from the inner shelf (not shown) of cannula housing 202 thus permitting the removal of obturator assembly 14 from cannula assembly (FIGS. 2 and 3) thereby leaving the cannula assembly within the incision to accept appropriate surgical instrumentation so as to conduct the desired surgery.

Figure 15:
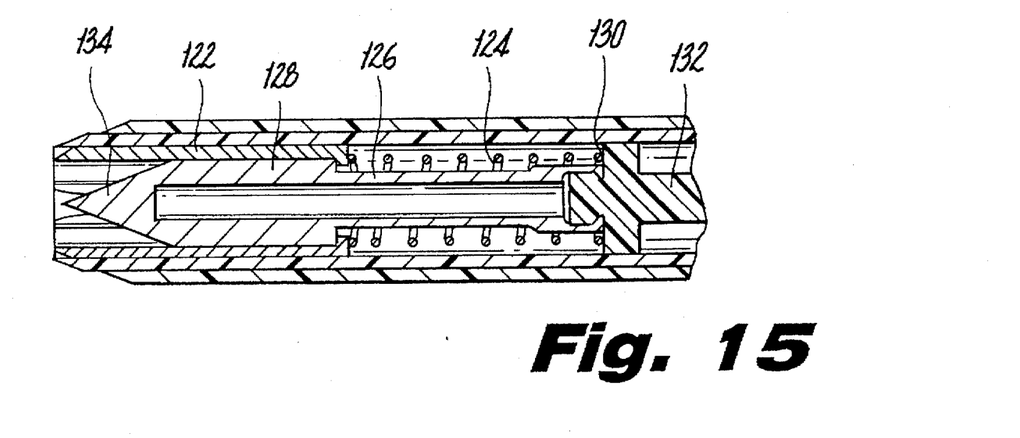
FIG. 15 is a side cross-sectional view of the distal end of another embodiment of the obturator assembly illustrating a protective guard positioned over the obturator penetrating tip.
Figure 16:
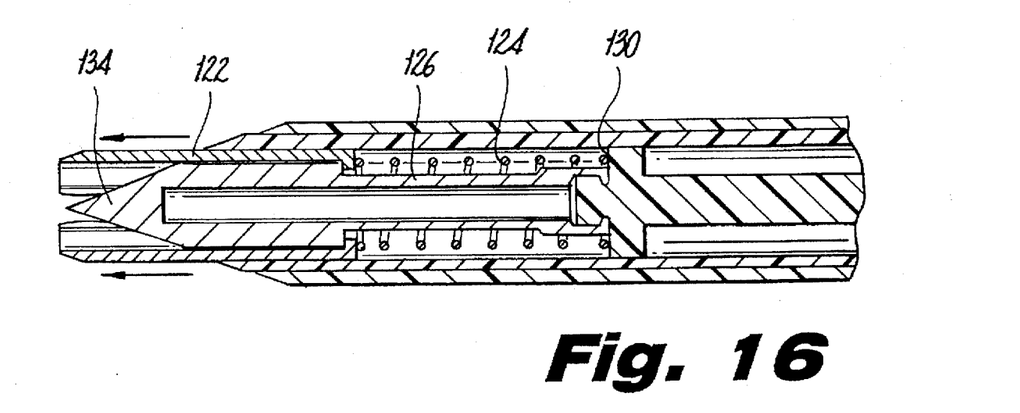
FIG. 16 is a view similar to the view of FIG. 15 illustrating the obturator portion in the armed position with the protective guard and obturator tip extending beyond the obturator and cannula sleeves.
Figure 17:
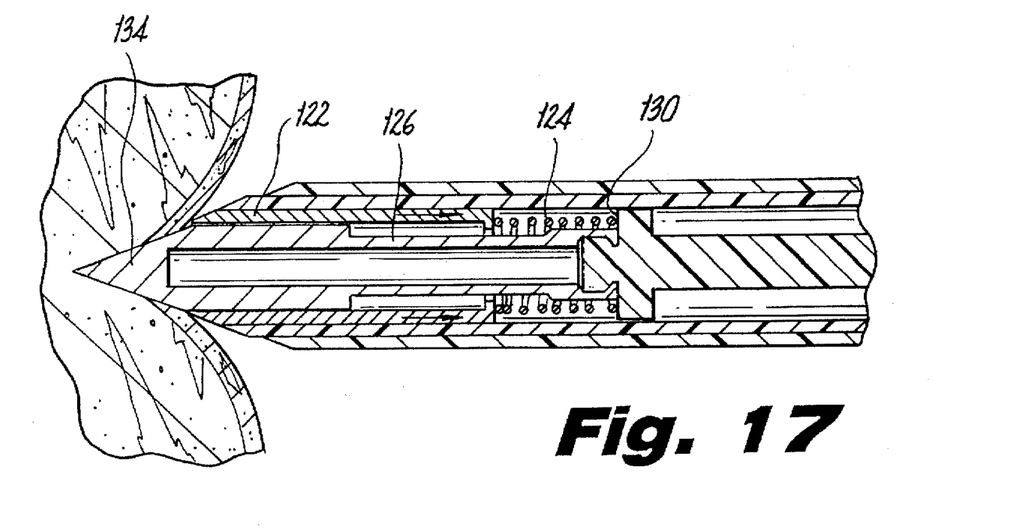
FIG. 17 is a view similar to the view of FIG. 16 illustrating the protective guard retracted upon application of the obturator against tissue.

Referring now to FIGS. 15–17, there is illustrated an alternative embodiment of the present disclosure. This embodiment incorporates an identical latch mechanism for releasably securing the obturator in its distal position as described in connection with the embodiment of FIG. 1 and is "armed" and "disarmed" in a similar manner. However, in accordance with this embodiment, elongated protective guard 66 is replaced with a truncated protective sleeve 122 as shown. A coil spring 124 is coaxially mounted about shaft portion 126 of penetrating member 128 and engages the distal face 130 of obturator shaft 132 and the proximal end of protective sleeve 122. Coil spring 124 normally biases protective sleeve 122 distally. With obturator shaft 64 distally advanced to its distal "armed" position shown in FIG. 16, application of the obturator against body tissue causes protective sleeve 122 to move proximally thereby exposing the penetrating tip 134 for penetrating action as shown in FIG. 17. Once the counterforce is removed, the protective sleeve 122 returns to its distal extended position under the influence of spring 124.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A trocar assembly, which comprises:
   a cannula including a cannula housing and a cannula sleeve extending from the cannula housing; and
   an obturator mounted to the cannula, the obturator including:
   an obturator housing;
   an elongated obturator portion mounted with respect to the obturator housing, the obturator portion including proximal and distal ends, and having a penetrating tip associated with the distal end for penetrating tissue, the obturator portion longitudinally moveable between a disarmed position wherein the penetrating tip is contained within the cannula sleeve and an armed position wherein the penetrating tip at least partially extends beyond the distal end of the cannula sleeve;
   retaining means for releasably retaining the obturator in the armed position;
   release means for releasing the retaining means to permit the obturator portion to return to the disarmed position, the release means actuable in response to forces exerted on the penetrating tip; and
   a protective guard coaxially mounted about the penetrating tip and being moveable relative to the penetrating tip between an extended position and a retracted position, wherein in the armed position of the obturator portion the protective guard moves to the retracted position in response to counterforce exerted by tissue on the protective guard during insertion through the tissue to thereby at least partially expose the penetrating tip for tissue penetration.

2. The trocar assembly according to claim 1 including guard biasing means for normally biasing the protective guard to the extended position thereof whereby, upon passing through the tissue, the protective guard is biased by the guard biasing means to the extended position.

3. The trocar assembly according to claim 2 wherein the guard biasing means includes a spring member.

4. The trocar assembly according to claim 1 including obturator biasing means for normally biasing the obturator portion to the disarmed position.

5. The trocar assembly according to claim 4 wherein the obturator biasing means includes a spring member.

6. The trocar assembly according to claim 4 including an obturator sleeve mounted to the obturator housing and extending distally therefrom.

7. The trocar according to claim 6 wherein the retaining means includes a latch mechanism, the latch mechanism including a latch mounted to the obturator portion and being configured and dimensioned to engage corresponding structure of the obturator sleeve to maintain the obturator portion in the armed position.

8. The trocar assembly according to claim 7 wherein the obturator sleeve includes an internal shelf and wherein the latch of the latch mechanism is configured and dimensioned to engage the internal shelf to thereby maintain the obturator shaft in the extended position.

9. The trocar assembly according to claim 8 wherein the obturator portion includes an obturator shaft, the penetrating tip being mounted to a distal end portion of the obturator shaft.

10. The trocar assembly according to claim 9 wherein the obturator shaft is reciprocally longitudinally movable between proximal and distal positions thereof when the obturator portion is in the armed position and further wherein the obturator shaft is spring biased to its distal position.

11. The trocar assembly according to claim 10 wherein the obturator shaft is adapted to assume its proximal position in response to a counterforce being applied to the penetrating tip and wherein upon removal of the counterforce the obturator shaft moves to its distal position.

12. The trocar assembly according to claim 11 wherein the release means includes a pawl, the pawl mounted to the obturator shaft and being configured and dimensioned to engage the latch upon movement of the obturator shaft distally from its proximal position to its distal position upon removal of the counterforce to thereby release the retaining means and permit the obturator portion to return to the disarmed position thereof.

13. An obturator assembly, which comprises:
    an obturator housing;
    an obturator sleeve connected to and extending from the obturator housing;
    an elongated obturator portion mounted with respect to the obturator housing, the obturator portion including proximal and distal ends, and having a penetrating tip associated with the distal end for penetrating tissue, the obturator portion longitudinally moveable between a disarmed position wherein the penetrating tip is contained within the obturator sleeve and an armed position wherein the penetrating tip at least partially extends beyond the distal end of the obturator sleeve;
    a releasable locking mechanism associated with the obturator portion, the releasable locking mechanism including a locking member engageable with one of the obturator sleeve and the obturator portion and moveable to an engaged position to releasably retain the obturator portion in the armed position, and a release member engageable with the locking member to move the locking member to a disengaged position thereof such that the locking member is disengaged from the one of the obturator sleeve and the obturator portion to thereby permit movement of the obturator portion to the disarmed position, the release member actuable to move the locking member to the disengaged position in response to forces exerted on the penetrating tip; and a protective guard coaxially mounted about the penetrating tip and being moveable relative to the penetrating tip between an extended position and a retracted position, wherein in the armed position of the obturator portion the protective guard moves to the retracted position in response to counterforce exerted by tissue on the protective guard during insertion through the tissue to thereby at least partially expose the penetrating tip for tissue penetration.

14. The obturator assembly according to claim 13 wherein the locking member is a latch mounted to the obturator portion and being configured and dimensioned to engage corresponding structure of the obturator sleeve when in the engaged position to maintain the obturator portion in the armed position.

15. The trocar assembly according to claim 14 wherein the obturator sleeve includes an internal shelf and wherein the latch is configured and dimensioned to engage the internal shelf to thereby maintain the obturator portion in the armed position.

16. The trocar assembly according to claim 14 wherein the release member is a pawl, the pawl mounted to the obturator portion and being configured and dimensioned to engage the latch to move the latch to the disengaged position.

* * * * *